(12) United States Patent
Nygren et al.

(10) Patent No.: US 9,965,939 B2
(45) Date of Patent: May 8, 2018

(54) SYSTEMS AND METHODS FOR MONITORING VIBRATIONS DURING TRANSPORTATION OF GOODS

(71) Applicant: Locus Solutions, LLC, Jupiter, FL (US)

(72) Inventors: Blair Nygren, Jupiter, FL (US); Rodney Parsons, Jupiter, FL (US)

(73) Assignee: LOCUS SOLUTIONS, LLC, Jupiter, FL (US)

( * ) Notice: Subject to any disclaimer, the term of this patent is extended or adjusted under 35 U.S.C. 154(b) by 0 days. days.

(21) Appl. No.: 15/254,449

(22) Filed: Sep. 1, 2016

(65) Prior Publication Data

US 2018/0061207 A1   Mar. 1, 2018

(51) Int. Cl.
| | |
|---|---|
| *G01N 19/08* | (2006.01) |
| *H04Q 5/22* | (2006.01) |
| *G08B 21/18* | (2006.01) |
| *G01P 15/18* | (2013.01) |
| *H04Q 9/00* | (2006.01) |
| *G06Q 10/08* | (2012.01) |

(52) U.S. Cl.
CPC ............ *G08B 21/182* (2013.01); *G01N 19/08* (2013.01); *G01P 15/18* (2013.01); *G06Q 10/0832* (2013.01); *H04Q 9/00* (2013.01); *H04Q 2209/40* (2013.01); *H04Q 2209/823* (2013.01)

(58) Field of Classification Search
None
See application file for complete search history.

(56) References Cited

U.S. PATENT DOCUMENTS

| | | |
|---|---|---|
| 5,313,848 A | 5/1994 | Santin et al. |
| 5,481,245 A | 1/1996 | Moldaysky |
| 6,122,959 A | 9/2000 | Hoshal et al. |

(Continued)

FOREIGN PATENT DOCUMENTS

| | | |
|---|---|---|
| JP | 2005014828 A | 1/2005 |
| JP | 2006062864 A | 3/2006 |
| KR | 101152352 B1 | 7/2012 |

OTHER PUBLICATIONS

Fischer, D. et al., Simulated in-transit vibration damage to packaged fresh market grapes and strawberries, Applied Engineering in Agriculture, vol. 8(3): May 1992, pp. 363-366.

(Continued)

*Primary Examiner* — Joseph Feild
*Assistant Examiner* — John Mortell
(74) *Attorney, Agent, or Firm* — Harness, Dickey & Pierce, P.L.C.

(57) ABSTRACT

A method for estimating a level of damage to perishable cargo during transportation of the cargo using data collected by a portable monitoring device. The method includes measuring vibrational data associated with the cargo. The vibrational data is monitored by a vibration sensor of the portable monitoring device. The method further includes incrementing a counter in the portable monitoring device in response to an amplitude of the measured vibrational data exceeding a predetermined threshold. The method also includes determining if the counter value exceeds a predetermined value, and generating an alert indicating damage to the cargo in response to determining the counter value has exceeded the predetermined value.

20 Claims, 9 Drawing Sheets

(56) References Cited

U.S. PATENT DOCUMENTS

| | | |
|---|---|---|
| 6,138,516 A | 10/2000 | Tillman |
| 6,873,936 B2 | 3/2005 | Reel et al. |
| 7,219,067 B1 | 5/2007 | McMullen et al. |
| 2003/0030565 A1* | 2/2003 | Sakatani ............... G01H 1/003 340/679 |
| 2006/0006987 A1* | 1/2006 | Hashimoto ......... G06K 7/0008 340/10.51 |
| 2006/0109106 A1 | 5/2006 | Braun |
| 2006/0158326 A1 | 7/2006 | Easley |
| 2008/0077989 A1 | 3/2008 | Bardsley et al. |
| 2008/0231438 A1 | 9/2008 | Curcio |
| 2010/0090822 A1 | 4/2010 | Benson et al. |
| 2010/0332407 A1 | 12/2010 | Grieve et al. |
| 2014/0049392 A1 | 2/2014 | Wagner |
| 2014/0069195 A1* | 3/2014 | Ledbetter ............... G01H 17/00 73/649 |
| 2014/0136430 A1 | 5/2014 | Pope |
| 2014/0180953 A1 | 6/2014 | Westcott et al. |
| 2015/0254600 A1* | 9/2015 | Murthy ............... G06Q 10/083 705/337 |
| 2016/0055453 A1* | 2/2016 | Cyman, Jr. ........ G06Q 10/0833 705/333 |
| 2016/0260059 A1* | 9/2016 | Benjamin .......... G06Q 10/0832 |

OTHER PUBLICATIONS

International Search Report regarding International Application No. PCT/US2017/047356, dated Oct. 23, 2017.
Written Opinion of the International Searching Authority regarding International Application No. PCT/US2017/047356, dated Oct. 23, 2017.

* cited by examiner

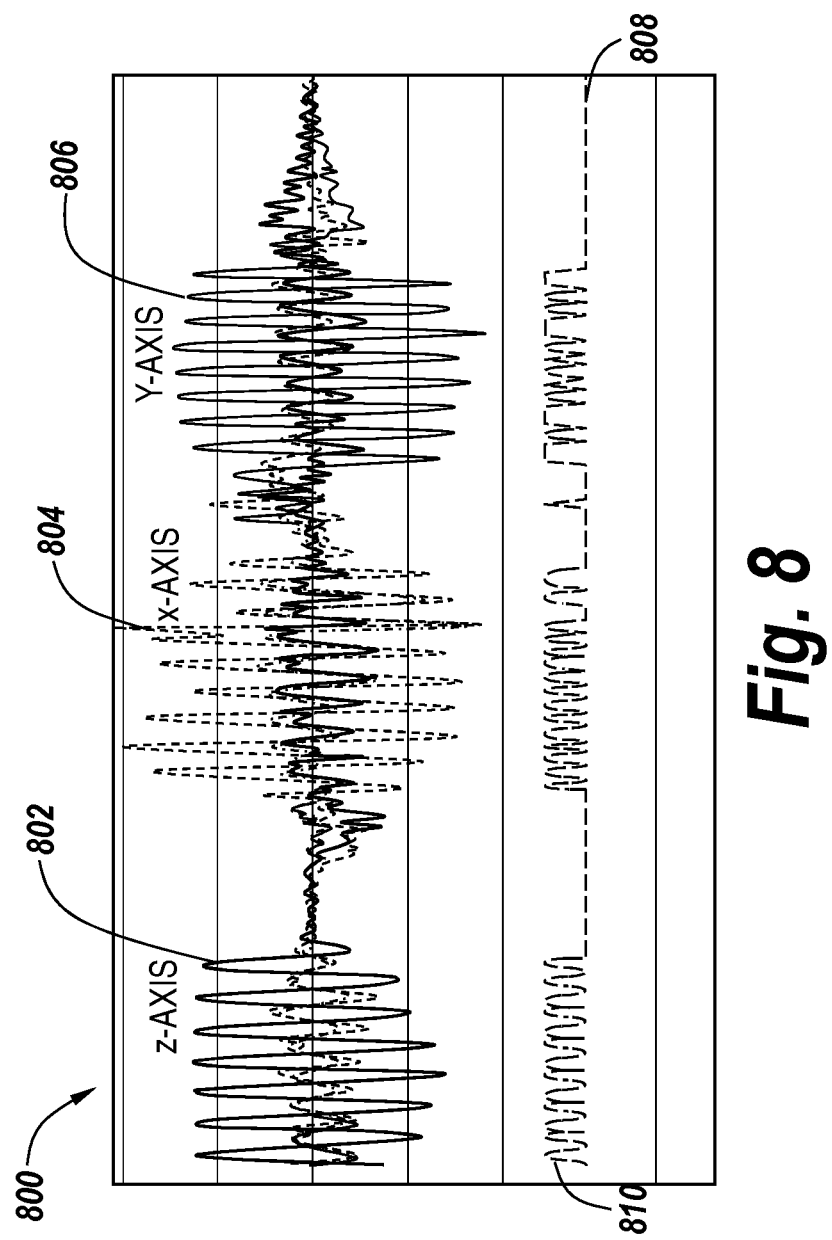

| | | | | | | |
|---|---|---|---|---|---|---|
| STATUS_REG_AUX | (0X00h) | FF | READ | WRITE | DEFAULT | |
| OUT_ADC1_L | (0X00h) | 00 | READ | WRITE | DEFAULT | |
| OUT_ADC1_H | (0X00h) | 00 | READ | WRITE | DEFAULT | |
| OUT_ADC2_L | (0X00h) | 00 | READ | WRITE | DEFAULT | |
| OUT_ADC2_H | (0X00h) | 00 | READ | WRITE | DEFAULT | |
| OUT_ADC3_L | (0X00h) | 00 | READ | WRITE | DEFAULT | |
| OUT_ADC3_H | (0X00h) | 00 | READ | WRITE | DEFAULT | |
| INT_COUNTER_REG | (0X00h) | 00 | READ | WRITE | DEFAULT | |
| TWP_CRG_REG | (0X10h) | 3F | READ | WRITE | DEFAULT | |
| CTAL_REG1 | (0X20h) | 00 | READ | WRITE | DEFAULT | |
| CTAL_REG2 | (0X20h) | 40 | READ | WRITE | DEFAULT | |
| CTAL_REG3 | (0X20h) | 00 | READ | WRITE | DEFAULT | |
| CTAL_REG4 | (0X20h) | 00 | READ | WRITE | DEFAULT | |
| CTAL_REG5 | (0X20h) | FF | READ | WRITE | DEFAULT | |
| CTAL_REG6 | (0X20h) | 00 | READ | WRITE | DEFAULT | |
| REFERENCE | (0X20h) | FF | READ | WRITE | DEFAULT | |
| STATUS_REG | (0X20h) | 00 | READ | WRITE | DEFAULT | |
| OUTX_L | (0X20h) | 00 | READ | WRITE | DEFAULT | |
| OUTX_H | (0X20h) | 00 | READ | WRITE | DEFAULT | |
| OUTY_L | (0X20h) | 00 | READ | WRITE | DEFAULT | |
| OUTY_H | (0X20h) | 00 | READ | WRITE | DEFAULT | |
| OUTZ_L | (0X20h) | 00 | READ | WRITE | DEFAULT | |
| OUTZ_H | (0X20h) | 00 | READ | WRITE | DEFAULT | |
| FIFO_CTRL_REG | (0X20h) | 00 | READ | WRITE | DEFAULT | |
| FIFO_SAC_REG | (0X20h) | 20 | READ | WRITE | DEFAULT | 902 |
| INT1_CFG | (0X30h) | 14 | READ | WRITE | DEFAULT | |
| INT1_SAC | (0X30h) | 15 | READ | WRITE | DEFAULT | |
| INT1_THG | (0X30h) | 37 | READ | WRITE | DEFAULT | |
| INT1_DURATION | (0X30h) | 00 | READ | WRITE | DEFAULT | |
| CLICK_CFG | (0X30h) | 00 | READ | WRITE | DEFAULT | |
| CLICK_SRC | (0X30h) | 00 | READ | WRITE | DEFAULT | |
| CLICK_THS | (0X30h) | 00 | READ | WRITE | DEFAULT | |
| TIME_LIMIT | (0X30h) | 00 | READ | WRITE | DEFAULT | |
| TIME_LATENCY | (0X30h) | 00 | READ | WRITE | DEFAULT | |
| TIME_WINDOW | (0X30h) | 00 | READ | WRITE | DEFAULT | |

Direct Communication

Address 00  Value 00  [Read] [Write]

All Registers Management  [Read All] [Write All] [Default All]

Note: "Default All" does not write default value reads registers (just stores it)

EASY CONFIGURATION

Fig. 9

SYSTEMS AND METHODS FOR MONITORING VIBRATIONS DURING TRANSPORTATION OF GOODS

BACKGROUND

Goods are transported around the world on a daily basis. Often, damage may occur to the goods due to vibrations associated with the transportation method. For example, perishable goods transported over road may experience vibrations across multiple frequencies and amplitudes, which can result in damage to the perishable goods. This is more pronounced in areas or countries where the roads are not maintained or are in poor condition. This damage from vibration has resulted in substantial loss in product and price by making the perishable goods unsalable, or, at best, damaged to the point of reducing the grade or overall quality of the products. However, it has been difficult to determine the exact cause of the damage, or the extent of the damage that was related to vibrations during portions of transport. Thus, it would be advantageous to have a system for monitoring and alerting a user when vibrations have reached the point of substantially damaging the goods.

SUMMARY

Some embodiments of the present disclosure relate to a method for estimating a level of damage to perishable cargo during transportation of the cargo using data collected by a portable monitoring device. The method includes measuring vibrational data associated with the cargo. The vibrational data is monitored by a vibration sensor of the portable monitoring device. The method further includes incrementing a counter in the portable monitoring device in response to an amplitude of the measured vibrational data exceeding a predetermined threshold. The method also includes determining if the counter value exceeds a predetermined value, and generating an alert indicating damage to the cargo in response to determining the counter value has exceeded the predetermined value.

A further embodiment of the present disclosure relates to a system for determining a level of damage to perishable goods during transport. The system includes an accelerometer configured to measure vibrations transmitted to the perishable goods during transport. The system further includes a processing circuit comprising a memory and a processor. The processing circuit is in communication with the accelerometer and configured to receive vibrational data associated with the measured vibrations from the accelerometer. The system also includes a processing circuit configured to generate an interrupt when an amplitude of the received vibrational data exceeds a predetermined threshold. The interrupt incrementing a counter value stored in the memory. The processing circuit is further configured to generate an alert in response to determining the counter value has exceeded a predetermined value.

A still further embodiment of the present disclosure includes a method of determining a level of damage to perishable cargo due to vibrations occurring during transport. The method includes measuring vibrational data using a vibration sensor attached to a container containing the perishable cargo and configured to measure an amplitude of the vibrations at each of a number of predetermined frequency ranges. The method also includes transmitting the vibrational data to a processing circuit of a portable monitoring device, and determining if the vibrational data exceeds a threshold value associated with damage occurring to the perishable cargo using the processing circuit of the portable monitoring device. The method additionally includes generating an interrupt signal for every occurrence of the threshold value being exceeded using the portable monitoring device and incrementing a counter in the portable monitoring device for every interrupt signal generated. The method includes determining if the counter value exceeds a first predetermined value within a predetermined time period, and generating an alert indicating a first level damage to the cargo in response to determining the counter value has exceeded the first predetermined value.

BRIEF DESCRIPTION OF THE DRAWINGS

The disclosure will become more fully understood from the following detailed description, taken in conjunction with the accompanying figures, wherein like reference numerals refer to like elements, in which:

FIG. 8 is a diagram representing a data readout of an accelerometer located on transported goods, indicating frequency and amplitude of vibrations applied to the transported goods;

FIG. 9 is a diagram representing an exemplary vibrational interrupt register readout indicating the number of times a vibration level was applied to transported goods that exceeded a predetermined threshold;

DETAILED DESCRIPTION

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Referring generally to the figures, systems and methods relating to the monitoring of goods during transportation is shown and described. Features of various embodiments of the present disclosure include, but are not limited to: determining at what vibrational frequencies and amplitudes damage may occur to goods during transport; monitoring vibrations associated with the transportation of goods; and assessing potential damage to the goods based on the detected vibrations and associated amplitudes. For example, an estimated percentage of damage to the goods being transported may be able to be determined based on the monitored vibrational frequencies and amplitudes. In some embodiments, an estimate of loss (e.g. amount of unsalable products at the end of the transport) may be able to be provided to a user, such as a transportation company, a shipper, of a buyer of the goods.

In some embodiments, a portable monitoring device may be used to monitor the frequency and amplitude of the vibrations that the goods are subjected to during transport. The portable monitoring device may be able to monitor the vibrations using an accelerometer or other vibration sensing device. In some examples, the portable monitoring device may further be able to determine the location of the transport vehicle, allowing for location data to be provided along with the vibrational data. The portable monitoring device may further communicate the vibrational data, along with various other types of data to a remote server where it can be further analyzed and transmitted to one or more users. In some examples, the remote server and/or the portable monitoring device may initiate an alarm when the vibrational frequencies and amplitudes indicate that a predetermined percentage of the goods are expected to be damaged.

Figure 1:
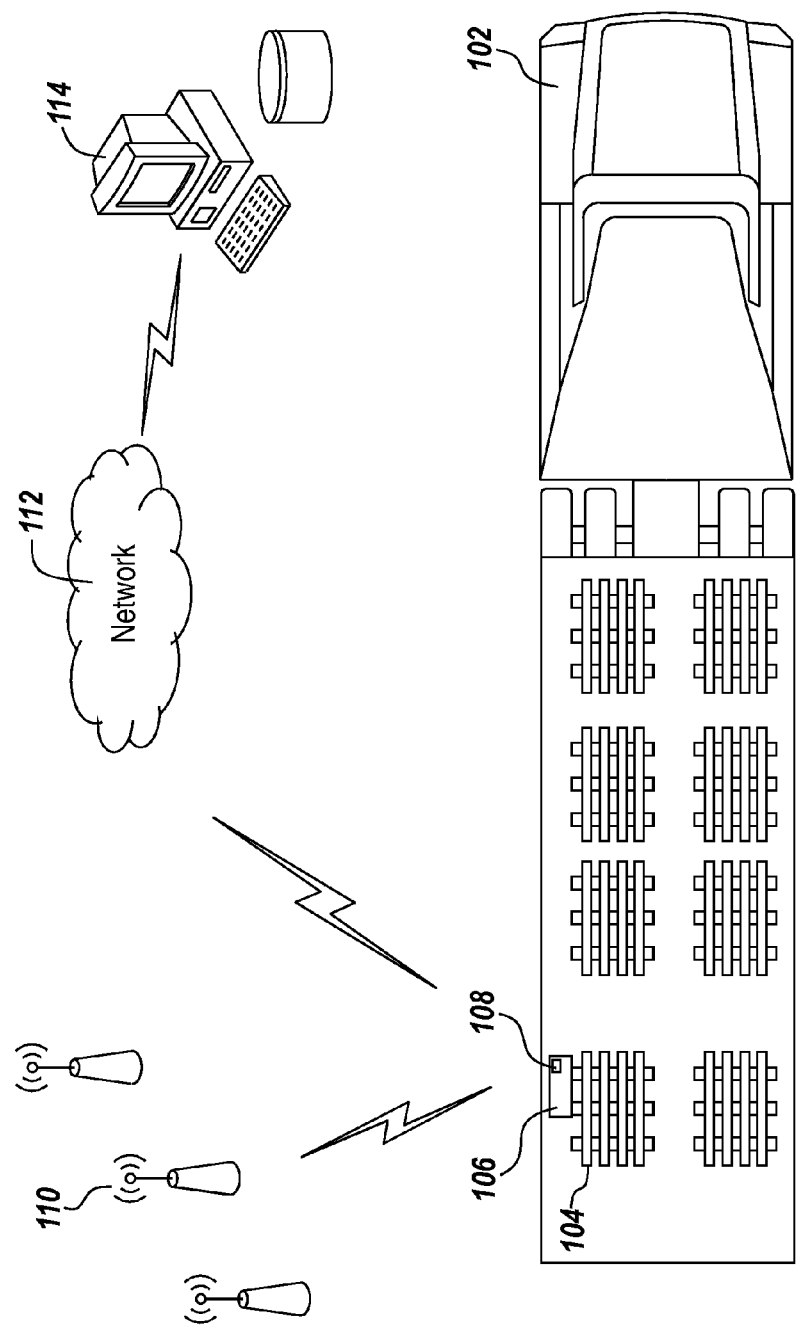
FIG. 1 is a diagram illustrating a portable monitoring device in a vehicle transmitting signals to a remote server, according to an exemplary embodiment.

Referring now to FIG. 1, a transport vehicle 102 is shown transporting goods 104. A portable monitoring device 106 is shown in transport vehicle 102 and is configured to be in communications with a remote server 114 via a network 112 and one or more cell towers 110. The remote server 114 may then use signals transmitted by the portable monitoring device 106 and relayed by the cell towers 110 to, for example, determine the location of the transport vehicle 102. In some embodiments, as shown in FIG. 1, the portable monitoring device 106 is coupled to goods 104 (e.g., fastened to a box housing the transported goods, to a pallet on which the goods are placed, affixed to the goods themselves, etc.). In some embodiments, the portable monitoring device 106 may be configured to operate within an enclosed space of the vehicle 102, such as a cargo area or enclosure. In other embodiments, the portable monitoring device 106 is coupled to the transport vehicle 102 in any other location, and may or may not be physically attached to the goods 104. It should be understood that the positioning of the portable monitoring device 106 in the transport vehicle 102 may vary without departing from the scope of the present disclosure.

The portable monitoring device 106 may include one or more sensors 108 coupled to and/or housed within the portable monitoring device 106. The sensors 108 may include an accelerometer, temperature sensor, ambient light sensor, or any other sensor configured to sense the condition or environment surrounding goods 104. The sensors 108 may generally be used to, for example, measure a temperature of cargo or near the cargo, to sense changes in the intensity of light in the cargo area (to determine if a cargo door is open), and to sense acceleration forces (to determine if vehicle 102 is in motion). The sensors may also be used to sense a frequency and magnitude of vibrations the goods 104 are subjected to during transit. In the embodiment of FIG. 1, the sensors 108 are shown housed within portable monitoring device 106; in other embodiments, the sensors 108 may be located in any other position within the transport vehicle 102, and may or may not be integrated with the portable monitoring device 106 (e.g., the sensors 108 may communicate wirelessly with the portable monitoring device 106 via a wireless connection).

The portable monitoring device 106 is shown communicating with the remote server 114 via the network 112 and multiple cellular towers 110. The network 112 may be or include any type of network (e.g., a cellular network or other a radio communication network, a WAN, a LAN, etc.) configured to transmit information between the portable monitoring device 106 and the remote server 114 via one or more of a variety of communications protocols. The multiple cell towers 110 are shown which transmit cellular signals to the portable monitoring device 106, which can be used to estimate the location of portable monitoring device 106. In some embodiments, cellular triangulation is used to estimate the location of the portable monitoring device 106. While the multiple cell towers 110 are shown in FIG. 1, it should be understood that, in some embodiments, other types of equipment (e.g., GPS satellites, other satellites) may be used, alone or in combination with the cellular signals, to estimate the location of the portable monitoring device 106 in the illustrated system.

Figure 2:
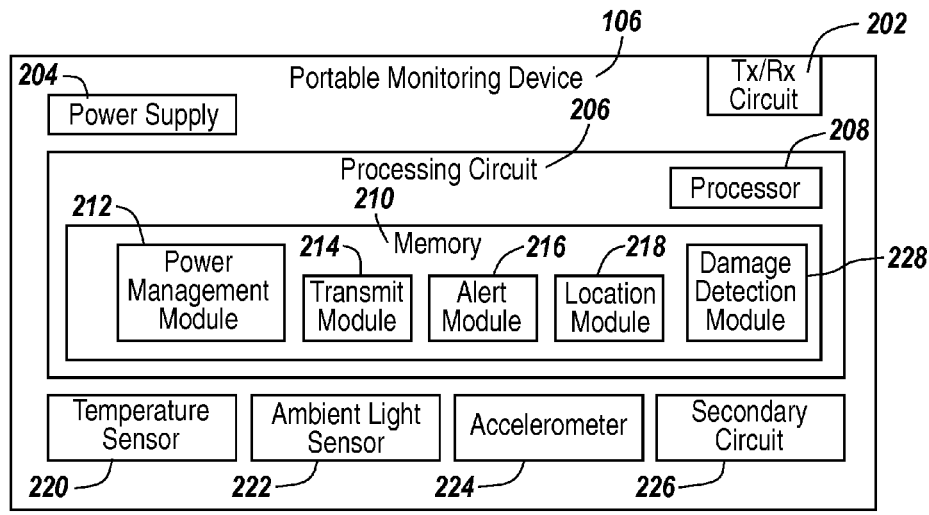
FIG. 2 is a detailed block diagram of the portable monitoring device of FIG. 1, according to an exemplary embodiment.

Referring now to FIG. 2, a detailed block diagram of the portable monitoring device 106 is shown, according to one embodiment. The portable monitoring device 106 is shown to generally include a transmit/receive circuit 202 configured to facilitate wireless communications with, for example, the remote server 114 and/or the multiple cell towers 110. The transmit/receive circuit 202 may include, for example, a cellular transceiver configured to receive cellular signals from the multiple cell towers 110 and transmit cellular signals to the multiple cell towers 110.

The portable monitoring device 106 further includes one or more sensors configured to provide sensor data, which can be used by portable monitoring device 106 and remote server 114 for generating alerts, monitoring goods, adjusting power management settings, and the like. For example, portable monitoring device 106 may include a temperature sensor 220 for detecting a current temperature level in the transport vehicle 102. The temperature sensor 220 may sense the temperature at a given time interval or schedule (e.g., every five minutes, every fifteen minutes, etc.). The temperature sensor data 220 may then be used to determine if a current temperature level may compromise the goods 104 (e.g., frozen or refrigerated food in a warm environment), if a refrigeration system of the transport vehicle 102 is malfunctioning, etc.

As another example, portable monitoring device 106 may include an ambient light sensor 222. The ambient light sensor 222 may sense ambient light inside of the transport vehicle 102. If a door of the transport vehicle 102 is opened, the ambient light sensor 222 may sense the increased ambient light inside the transport vehicle 102, and the resulting sensor data may be used to indicate that a user at the destination has opened the door, that the door should not be open and something is wrong, and the like. The ambient light sensor 222 may be configured to sense an increase or decrease in ambient light when it occurs, or may be configured to sense ambient light at a given time interval or schedule (e.g., every five minutes, every fifteen minutes, etc.).

In one embodiment, the portable monitoring device 106 includes an accelerometer 224. The accelerometer 224 may sense acceleration forces to determine if the transport vehicle 102 is in motion or not. In some embodiments, the accelerometer 224 may generate signals representative of a sensed vibration. The signals may be indicative of a duration and/or amplitude/intensity of vibration. The vibration data of accelerometer 224 may be used to determine the rate at which transport vehicle 102 is moving (e.g., relative or absolute rate), based on the duration and/or intensity of vibration detected. In one embodiment, the vibration data of the accelerometer 224 is used to determine a percentage of damage to the goods 104. Particularly where the goods 104 are perishable food items such as fruits and vegetables. The process of determining damage rates to the goods 104 is described in more detail below. In other embodiments, the accelerometer 224 may generate other signals indicative of movement, such as g-force data, orientation data, shock data, etc. The portable monitoring device 106 may further include various other sensors, and a sensor interface for communicating via a wired or wireless connection with sensors located remotely from portable monitoring device 106.

Portable monitoring device 106 is shown to include a processing circuit 206 including a processor 208 and memory 210. With respect to FIG. 3, remote server 114 is shown to include a processing circuit 304 including a processor 306 and memory 308. Processors 208, 306 may be general purpose or specific purpose processors, application specific integrated circuits (ASIC), one or more field programmable gate arrays (FPGAs), a group of processing components, or other suitable processing components. Processors 208, 306 may be configured to execute computer code or instructions stored in memories 210, 308 or received from other computer readable media (e.g., CD-ROM, network storage, a remote server, etc.) to perform one or more of the processes described herein. Memories 210, 308 may include one or more data storage devices (e.g., memory units or devices) configured to store data, computer code, executable instructions, or other forms of computer-readable information. Memories 210, 308 may include random access memory (RAM), read-only memory (ROM), hard drive storage, temporary storage, non-volatile memory, flash memory, optical memory, or any other suitable memory for storing software objects and/or computer instructions. Memories 210, 308 may include database components, object code components, script components, or any other type of information structure for supporting the various activities and information structures described in the present disclosure. Memories 210, 308 may be communicably connected to processors 208, 306 via processing circuits 206, 304 and may include computer code for executing (e.g., by processors 208, 306) one or more of the processes described herein.

Referring again to FIG. 2, the memory 210 is shown to include various modules for controlling the operation of the portable monitoring device 106. The various modules can include a power management module 212, a transmit module 214, an alert module 216, a location module 218, and a damage detection module 228. In one embodiment, the power management module 212 is configured to control the activity of the portable monitoring device 106 for power conservation and/or communication management purposes. For example, the portable monitoring device 106 may include a power supply 204, which may generally be or include a battery or other power source that may become depleted over time. The power management module 212 may adjust the activities of the portable monitoring device 106 based on the level of the power supply 204 available in the device at a given point in time. The power management module may further adjust the activities of the portable monitoring device 106 based on the general power usage of the portable monitoring device 106. For example, the activities of the portable monitoring device 106 may be adjusted to ensure that enough power remains for the duration of a scheduled trip. Such activities may include a transmission schedule (e.g., adjusting a schedule to cause the device to transmit a signal once every four hours instead of once every hour). Such activities may further include continuously monitoring the battery level and increasing or decreasing the transmission power of the device based on the remaining battery level.

The transmit module 214 is configured to control transmissions of the portable monitoring device 106 via the transmit/receive circuit 202. In one example, the transmit module 214 may receive sensor data and transmit the sensor data along with signal data (e.g., data representing one or more characteristics of the received cellular signals) and/or other device data for transmission to the remote server 114. In some embodiments, the sensor data can be processed at transmit module 214, or more generally portable monitoring device 106, to determine the location of portable monitoring device 106. In other embodiments, the sensor data is transmitted by the remote server 114, which may then determine the location of the portable monitoring device 106.

The transmit module 214 may further be configured to generate a transmission on a schedule (e.g., once every ten minutes, once every hour, etc.). The transmit module 214 may modify the transmission schedule based on various factors. For example, the transmit module 214, alone or in coordination with power management module 212, may vary the transmission power of transmissions sent to remote server 114 (e.g., if the power supply is running low, if an warning is being transmitted, if an end of trip situation is detected), or may use different frequency channels for transmissions to different devices. As another example, the transmission schedule may be modified based at least in part on a remaining battery life. As another example, if vehicle movement is not detected by accelerometer 224, transmit module 214 may transmit signals less often. As another example, the transmission schedule may be adjusted based on the location of the portable monitoring device 106 (e.g., if the vehicle is a boat and the location is a body of water, the device may transmit signals less often). In some embodiments, the goods in transit may switch transport vehicles (e.g., from a truck to boat or vice versa, from one truck to another), and transmit module 214 may use information relating to the switch of vehicles to adjust the transmission schedule.

Alert module 216 is configured to generate an alert or warning based on a current condition relating to transport vehicle 102. For example, alert module 216 may receive a temperature reading from temperature sensor 220 and determine that the temperature is hazardous to the goods. Alert module 216 may then generate a signal to be transmitted to remote server 114. As another example, alert module 216 may receive an indication of increased ambient light from ambient light sensor 222, and determine that an alert should be generated (e.g., because increased ambient light would indicate the opening of a door that should not be open). As another example, alert module 216 may receive a low power indication from power management module 212, and may provide the indication to remote server 114. Further, alert module 216 may provide an indication to if (and how) the operation of portable monitoring device 106 changed in response to the low power situation. In some embodiments, alert module 216 may generate an alert based on a determination by location module 218 that a current location of device 106 is within, or has just entered or left, one or more defined geographic areas (e.g., areas around a starting location, destination, one or more checkpoint locations, ports, etc.). The activities of the alert module 216 are described in greater detail in FIG. 4.

The location module 218 is configured to determine, alone or in combination with remote server 114, a current location of the portable monitoring device 106 and the transport vehicle 102. In some embodiments, the location module 218 receives cellular signals from the multiple cell towers 110 and uses the received signals to calculate a location of the transport vehicle 102. For example, the location module 218 may use cellular triangulation using the multiple cell towers 110 providing the strongest signal to the portable monitoring system 106. The location module 218 may determine characteristics of the cell signals and use the characteristics to calculate the location. For example, the location module 218 may calculate a received signal strength indication (RSSI) of the signals and use the RSSI to calculate the location of the transport vehicle 102 (e.g., based on a determination that stronger signals indicate a closer proximity to a known location of a cell tower, and weaker signals indicate a farther proximity from the cell tower). In some embodiments, cellular signal characteristics other than RSSI may be used alone or in combination with RSSI.

In some embodiments, the location module 218 may use other types of transceivers or sensors to help determine a location of the portable monitoring device 106, alone or in combination with cellular signals. For example, the portable monitoring device 106 may include a GPS transceiver configured to receive one or more GPS signals and determine a position of the portable monitoring device 106 using the signals. In some examples, portable monitoring device 106 may include a Wi-Fi transceiver, Bluetooth transceiver, RFID transceiver, or other long or short-range communication interface, and may determine a position of the portable monitoring device 106 using the data received via such communication interfaces. In one embodiment, the portable monitoring device 106 uses cellular signals as a primary source for determining the position of the portable monitoring device 106, and may use location data received from other secondary sources to confirm and/or refine the location determined using the cellular signals.

In one embodiment, the location module 218 calculates the estimated location of the transport vehicle 102, and the estimated location may be transmitted to the remote server 114. In another embodiment, the location module 218 may determine or retrieve signal characteristics based on transmissions from the multiple cell towers 110, and provide the signal characteristics to the remote server 114. The remote server 114 may then calculate the estimated location of the transport vehicle 102.

In some embodiments, the location module 218 may determine if the transport vehicle 102 has moved since a previous time when the location of transport vehicle 102 was determined. For example, the location module 218 may use accelerometer data to determine if the transport vehicle 102 has moved. Accelerometer data may indicate a vibration amplitude and duration that was sensed by the accelerometer 224. The location module 218 may determine if the amplitude and/or duration of the vibration exceeds a threshold indicating movement (e.g., indicating that the transport vehicle 102 was in motion since the last location update.) As another example, the location module 218 may determine the location and identity of one or more of the multiple cell towers 110 providing the signal to the portable monitoring device 106. The location module 218 may compare the signals received from the multiple cellular towers 110 used to provide the previous transmission and the current transmission. If one or more of the cellular towers 110 are different, the location module 218 determines that transport vehicle 102 moved, because at least one different cellular tower 110 provided a stronger signal to the portable monitoring device 106. In one embodiment, the location module 218 compares signal characteristics, such as RSSI values, to corresponding characteristics from previously received signals, and if the characteristics change by at least a threshold value, the location module 218 determines that the portable monitoring device 106 has moved. In some embodiments, as described in further detail below, the location module 218 may determine whether movement has occurred based on a combination of both the cellular signals and movement data from an accelerometer or other movement detection device. In some embodiments, the location module 218 may transmit cellular signal characteristic data and movement data from the accelerometer 224 to the remote server 114, and the remote server 114 may determine whether or not movement of the portable monitoring device 106 has occurred.

In one embodiment, the damage detection module 228 is configured to determine a level of damage to the goods being transported. For example, the damage detection module 228 may provide an analysis indicating a percentage of damage that may have occurred during transport. In some embodiment, the damage detection module 228 may receive data from the accelerometer 224, such as vibrational data, and determine an estimated amount of damage based on the received data, as described in more detail below. Further, the damage detection module 228 may be configured to communicate with the location module 218 to provide information regarding locations where damage may have occurred. Further, the damage detection module 228 may be configured to communicate with the alert module 216 to generate an alert when the amount of estimated damage exceeds a threshold. In one embodiment, the damage detection module 228 communicates an estimated percentage of damage to the alert module 216. The alert module 216 is then further configured to provide the estimated percentage of damage in the alert. For example, the alert may report a percentage of damage in increments from 0% to 100%, where 100% indicates that the damage is 100%. Thus, if the alert states 20%, then it is estimated that 20% of the cargo is damaged. Conversely, the alert may state the damage to the cargo as a percentage of the cargo that is not damaged. For example, 100% would indicate that all of the cargo is salable, while 20% would indicate that only 20% of the cargo is salable. The alert reporting type may be configurable by the user. Additionally, the damage detection module 228 may be configured to communicate with the transmit module 214 to transmit data associated with the estimated damage to the remote server 114. For example, the damage detection module 228 may transmit the estimated percentage of damage to the remote server 114.

In some embodiments, the portable monitoring device 106 may include a secondary communication circuit 226 configured to enable communication with one or more other devices (e.g., other portable monitoring devices) in proximity to the portable monitoring device 106 (e.g., devices in the same vehicle, on or in one or more other adjacent vehicles carrying related cargo). The portable monitoring device 106 may include a secondary radio transceiver configured to communicate with devices using a short, medium, or long-range communication protocol. One or more of various communication protocols may be utilized, such as Bluetooth, Wi-Fi, etc. In some embodiments, a communication protocol, such as those based on the IEEE 802.15.4 standard, is utilized. In some embodiments, a proprietary communication protocol may be utilized. In some embodiments, the secondary communication circuit 226 may be separate from transmit/receive circuit 202. In some embodiments, the secondary communication circuit 226 may be integrated with the transmit/receive circuit 202 (e.g., such that the transmit/receive circuit 202 includes one or more circuits capable of communicating both with one or more local devices and with one or more of the multiple cell towers 110).

In some embodiments, the secondary communication circuit 226 may be configured to communicate with devices across multiple frequency bands or channels. For example, the secondary communication circuit 226 may include a first transceiver configured to communicate with devices on a first frequency band (e.g., 2.4 GHz) and a second transceiver configured to communicate with devices on a second frequency band (e.g., 433 MHz).

In some examples, the secondary communication circuit 226 may include dedicated hardware components configured to communicate with particular components across different frequencies. In other examples, the secondary communication circuit 226 may be at least partially software-defined, such that the devices with which the secondary communication circuit 226 interacts and/or the frequencies upon which the secondary communication circuit 226 communicates may be modified using software, without modifying hardware.

The other devices discussed above may include one or more sensors configured to communicate with the secondary communication circuit 226 through a communication interface coupled to the sensors (e.g., a radio circuit). For example, a radio circuit may include one or more interfaces to which one or more sensors are coupled. The radio circuit may be configured to transmit data collected by the sensors to the portable monitoring device 106, which may process the data to generate alerts and/or transmit the data to the server 114. In one embodiment, the radio circuit is configured to receive data from multiple accelerometers located within the transport vehicle 102. In other examples, the radio circuit may include one or more preconfigured interfaces configured to receive data from other sensors, such as temperature sensors, ambient light sensors, movement sensors, etc. In some embodiments, the radio circuit may be reconfigurable to adapt to different types of sensor input through software and/or simple hardware reconfigurations. For example, in some embodiments, the radio circuit may include a software-defined radio module configured to implement one or more processing functions through the use of processor-readable instructions. Such a radio circuit may include one or more interfaces configurable to receive input from multiple different types of sensors. Adaptability to different sensor input may allow for easy and inexpensive implementation of monitoring for a wide variety of applications related to the transportation of the goods in the vehicle.

Figure 3:
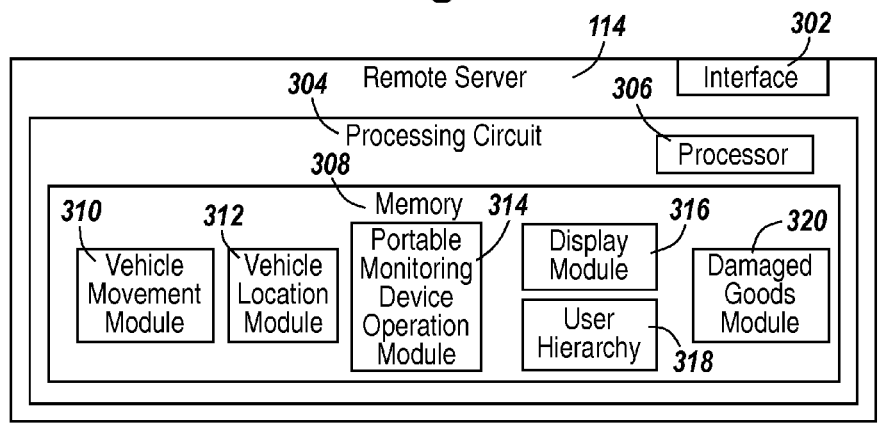
FIG. 3 is a detailed block diagram of the remote server of FIG. 1, according to an exemplary embodiment.

Referring now to FIG. 3, a detailed view of a remote server, such as remote server 114 is shown, according to one embodiment. The remote server 114 is generally configured to receive signals transmitted by the portable monitoring device 106 and to provide support to the portable monitoring device 106. The remote server 114 is further configured to provide information to one or more users via a display module 316. The remote server 114 is further shown to include an interface 302. The interface 302 may be configured to wirelessly receive data via the network 112. In one embodiment, the interface 302 is a wireless communication interface. The interface 302 may be any type of wireless communication interface configured to receive signals from portable monitoring device 106. The remote server 114 includes a processing circuit 304 including a processor 306 and memory 308 as described above.

As described above, some of the activities of the location module 218 of the portable monitoring device 106 may be executed at the remote server 114. For example, the memory 308 is shown to include a vehicle movement module 310 configured to determine if the transport vehicle 102 has moved from a previous location. The vehicle movement module 310 may determine that the transport vehicle 102 has moved based on accelerometer data and/or cell tower information, as described above. Further, memory 308 is shown to include a vehicle location module 312. The vehicle location module 312 is configured to calculate the current location of the transport vehicle 102 and/or receive the current location from the portable monitoring device 106. While in some embodiments the vehicle location and/or motion is calculated using the location module 218 of the portable monitoring device 106, in other embodiments some or all of the calculations may occur using the vehicle movement module 310 and the vehicle location module 312. In such an embodiment, the remote server 114 is configured to wirelessly receive input from the portable monitoring device 106 via the network 112, including signal characteristics (e.g., RSSI) of signals received at the portable monitoring device 106 from the multiple cell towers 110, accelerometer data, and/or other sensor and/or communication interface (e.g., transceiver) data.

As described above, the location module 218 and/or the vehicle movement module 310 may use RSSI data to determine if the transport vehicle 102 has moved. For example, if the same three cell towers 110 provided the strongest signals to the portable monitoring device 106 two times in a row, the RSSI values of the signals may be compared to one another. If the difference in RSSI values exceeded a threshold (e.g., 10%), it may be determined that the transport vehicle 102 is moving, as the position of the portable monitoring device 106 has changed relative to the cell tower(s). If one or more of the cell towers 110 associated with the set of strongest received signals changes, this may be interpreted as indicating vehicle movement in some embodiments.

The location of the transport vehicle 102 may be used by the remote server 114 to adjust the operation of the portable monitoring device 106. For example, the current vehicle location may be used to determine if an alert should be generated and transmitted to the portable monitoring device 106 (e.g., if sensor data in combination with the vehicle location indicates a potentially hazardous situation, or if the data indicates that the goods 104 may be damaged soon). As another example, the current vehicle location may be used to trigger a transmission to the portable monitoring device 106 to enter a power conservation mode (e.g., if the vehicle is close to its destination, then power conservation may not be used; if the vehicle is far away from its destination, then the power conservation features may be activated).

The portable monitoring device operation module 314 may provide instructions to portable monitoring device 106. For example, if a warning or alert was generated by the portable monitoring device 106, the portable monitoring device 106 may be instructed to transmit sensor data more often. As another example, if a low battery or low power situation is detected on the portable monitoring device 106, the portable monitoring device may be instructed to enter a mode in which it transmits signals to remote server 114 less often. The portable monitoring device operation module 314 may be configured to determine a new transmission schedule and to otherwise adjust the operation of portable monitoring device 106.

The display module 316 is configured to generate data for display to one or more users (e.g., a carrier, a recipient, a shipper, etc.) relating to the transport vehicle 102 location and status. For example, the display module 316 may generate maps, tables, or other visual data that illustrate the location of the vehicle, the vibrational data monitored during transport, and/or other characteristics of the cargo. The display may indicate the position of the transport vehicle 102 at different times, if and where the transport vehicle 102 has stopped moving, and/or other general trip properties (e.g., trip duration, distance covered and distance left, etc.). The display module 316 may further generate data relating to one or more alarms or warnings generated by portable monitoring device 106 or remote server 114 (e.g., vibrational levels exceeded, excess damage to product, etc.). The display module 316 may further generate data relating to a power supply status of the portable monitoring device 106 (e.g., if the power supply is low enough such that updates from portable monitoring device 106 will become less frequent in the future). The display module 316 may update at regular intervals (e.g., every 15 minutes, every time the remote server 114 receives a signal from the portable monitoring device 106) or may update as warranted (e.g., when the transport vehicle 102 has arrived at a destination, upon generation of an alert or warning, etc.). It should be understood that the display module 316 may generate any type of report (e.g., images, text, email, etc.) for any type of device (e.g., laptop, desktop, mobile device, tablet, etc.), and may generate the report for different users (e.g., a first responder, a supervisor) depending on the nature of the report. The data generated by the display module 316 may be provided to one or more user devices, for example, via a network (e.g., using an app, a web-based interface, etc.).

The remote server 114 is further shown to include a user hierarchy 318. In one embodiment, the remote server 114 stores a user hierarchy 318, and may receive updates to the user hierarchy 318 from another source. In another embodiment, the remote server 114 may be configured to both store and maintain or update the user hierarchy 318. While the user hierarchy 318 is shown in remote server 114, in other embodiments, user hierarchy may alternatively or additionally be stored in portable monitoring device 106.

The user hierarchy 318 may indicate a plurality of users responsible for supervising or managing the transport of goods 104 via the transport vehicle 102. For example, the user hierarchy 318 may include one or more users assigned to monitor the vehicle, and one or more supervisors assigned to receive alerts or warnings related to vehicle operation. Different users in the user hierarchy may have different levels of responsibility related to operation of the transport vehicle 102 and the goods 104. In some embodiments, the user hierarchy 318 may be a list detailing the responsibilities and may indicate to the remote server 114 a list of users for which display data, alerts, etc. should be generated.

In one embodiment, the remote server 114 may generate a report for a first user (or users) during normal operation of the transport vehicle 102. If an alert or warning is generated by the portable monitoring device 106, the remote server 114 may generate a display indicating the alert to the first user. The remote server 114 may then receive confirmation of receipt of the alert by the first user, or confirmation that the first user has addressed the alert. The remote server 114 may, if it does not receive a confirmation, generate an alert for a second user (e.g., a supervisor of the first user, a backup user, etc.). The user hierarchy 318 may be used by the remote server 114 to determine which users should be given which alerts. For example, one type of alert (e.g., ambient light increase) may be given to a first user while another type of alert (e.g., excess vibration) may be more appropriate for a second user.

The remote server 114 is further shown to include a damaged goods module 320. In one embodiment, the damaged goods module 320 may receive an estimate of the damage to the goods being transported from the damage detection module 228. In other embodiments, the damaged goods module 320 may receive data from the damage detection module 228 related to damage to the goods, and may perform a calculation to determine the amount of damage to the goods. In further embodiments, the damaged goods module 320, upon receiving the estimate of the damage to the goods from the damage detection module 228, may generate a report illustrating the estimated amount of damage to the goods. The report may include the estimated percent of damage to the goods, the associated impact of salability of the goods, the location where the damage occurred, the remaining time until the goods arrive at the destination, and an estimate of additional expected damage based on historical analysis.

Referring generally to FIGS. 2-3, it should be understood that the various activities of portable monitoring device 106 may be executed by the remote server 114, and vice versa. The portable monitoring device 106 and the remote server 114 may or may not coordinate with one another to generally implement the processes described herein.

Figure 4:
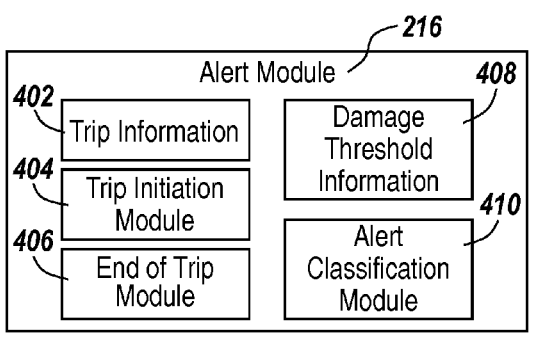
FIG. 4 is detailed block diagram of the alert module shown in FIG. 2, according to an exemplary embodiment.

Referring to FIG. 4, the activities of the alert module 216 are shown in greater detail, according to one embodiment. The alert module 216 may generate alerts based on various sensor data and location data received at the portable monitoring device 106. For example, the alert module 216 is shown to include trip information 402. The trip information 402 may include a planned route and/or destination of the transport vehicle 102 and location data relating to the route. If the transport vehicle 102 has arrived or is in the same geographic area of the destination (based on location data from location module 218), alert module 216 may suppress some or all possible alerts. For example, if a temperature is rising in transport vehicle 102, but the vehicle has reached its destination, an alert may be suppressed since the temperature increase may not impact the goods since the goods have arrived (or are currently being unloaded from the vehicle).

In some embodiments, the alert module 216 includes an end of trip module 406 to determine if the transport vehicle 102 has reached its destination, based on the trip information 402, location information, and/or other information. In some embodiments, the alert module 216 generates an alert to send to the remote server 114 that indicates that the goods have arrived at their destination. The alert module 216 may further send the information to the power management module 212, which may then be configured to power down the various sensors of the portable monitoring device 106

(e.g., when monitoring of the goods is no longer needed). In some embodiments, a SIM card (or other removable memory device) coupled to the transmit/receive circuit 202 of the portable monitoring device 106 (e.g., the cellular transceiver) may be deactivated upon receiving the indication that transport vehicle has arrived at the destination.

The end of trip module 406 may further use other sensor data to determine the end of the trip. For example, the end of trip module 406 may utilize temperature data from temperature sensor 220. If the temperature suddenly increased by a significant amount (e.g., frozen food removed from the transport vehicle), end of trip module 406 may check to see if the vehicle is at or near its destination. If so, it may be determined that the temperature increase is the result of the goods reaching their destination (e.g., the result of the a cargo area door being opened to unload the goods) and not an error of the cooling system of the transport vehicle or other problem. As another example, ambient light data from the ambient light sensor 222 may be used. If the ambient light suddenly increases by a significant amount (e.g., goods being removed from the vehicle into the sunlight), it may be determined whether the location of the transport vehicle 104 is at the destination, or another known checkpoint. If so, it may be determined that the goods are being unloaded at their destination. If not, an alert may be raised, as an unexpected opening of a cargo area could indicate tampering with or theft of the goods. As another example, accelerometer data from accelerometer 224 may be used. If the accelerometer no longer reports vibration (indicating the vehicle has stopped moving), it may be determined that the goods have arrived at their destination, instead of determining there is an issue with the transport vehicle or that the transport vehicle is idling near a dock waiting for a dock slot to open. As yet another example, the transmit/receive circuit 202, the secondary circuit 226, and/or another circuit (e.g., a communication circuit, such as a radio frequency communication device) may be configured to communicate with beacons or other signal transmission devices located at or near a destination (e.g., mounted on or near a loading dock). The portable monitoring device 106 and/or the remote server 114 may determine the cargo has reached the destination in response to receipt of a signal from the beacon, alone or in combination with determining that the location of portable monitoring device 106 is near the destination location. Any combination of location data, trip information, temperature data, ambient light data, accelerometer data, and/or other sensor data may be used to determine an end of trip scenario.

In some embodiments, the end of trip module 406 may, upon reaching the destination, automatically generate an alert and/or report to send to the remote server 114 indicating the trip has concluded. In response to the alert, portable monitoring device 106 and/or remote server 114 may generate a summary report providing information relating to the trip, such as a summary of one or more locations over the course of the trip, or one or more conditions relating to the goods (e.g., vibrational data). For example, the portable monitoring device 106 and/or the remote server 114 may generate a report indicating information about the number of times a vibration amplitude for one or more frequencies occurred over the trip. In some embodiments, the summary report may be provided to a user, such as the shipper, receiver, and/or carrier. In some embodiments, the report may be configured to fulfill one or more reporting requirements, such as FDA or other governmental/regulatory reporting requirements.

In some embodiments, the alert module 216 includes a trip initiation module 404 configured to determine when the transport vehicle 102 has started a trip (or has started a certain portion or segment of the trip). The trip initiation module 404 may receive an indication that the transport vehicle 102 is currently stopped, and may check location data and sensor data to determine when the transport vehicle 102 begins moving. For example, when the transport vehicle 102 begins moving, the accelerometer 224 may detect the vibrations, which may be used by trip initiation module 404 to determine that the trip has started (e.g., if the location is at or near a known starting location). In some embodiments, other sensors may be used alone or in combination with the accelerometer 224, such as the light sensor 222 (e.g., detecting when a door has been closed prior to moving, suggesting cargo has just been loaded/inspected) and/or the temperature sensor 220 (e.g., detecting a higher temperature that has begun to drop, which may indicate the cargo is loaded and the door has been closed, allowing refrigeration to begin). The trip initiation module 404 may be used by the alert module 216 to determine when to begin checking for alerts (e.g., ignoring false alerts generated by sensor data before beginning the trip).

An alert may be generated by the alert module 216 based on, for example, vibration frequencies and levels. If the number of times that vibrational levels exceeded a given value, an alert is generated. This will be described in more detail below. The alert module 216 is shown to include a damage threshold information 408. For example, damage threshold information 408 may include counters associated with one of more vibrational frequencies. The damage threshold information 408 may include a number of times a vibration at a particular frequency exceeded a predetermined value. In some embodiments, the damage threshold information 408 may generate an alert when the number of occurrences exceeds a predetermined number. In some embodiments, the generated alert may provide an estimated percentage of damage to the cargo.

Figure 5:
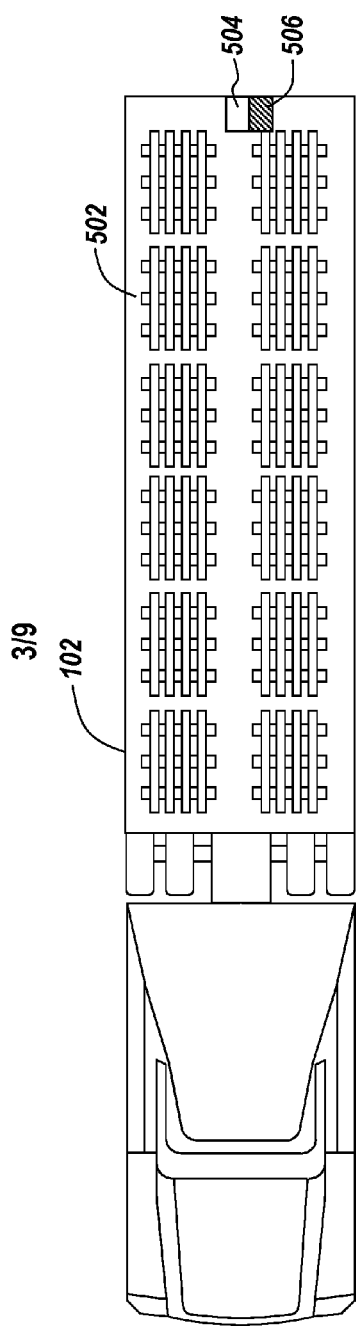
FIG. 5 is a diagram illustrating a possible mounting location for a portable monitoring device in a vehicle for monitoring damage to perishable goods from a top down view of the vehicle.

Turning now to FIG. 5, a top-down view of the transport vehicle 102 is shown. The transport vehicle 102 is shown to include a number of shipping containers 502. In one embodiment, the shipping containers 502 are stackable pallets. However, the shipping containers 502 may include stackable boxes, crates, or other applicable packaging. In one embodiment, the shipping containers 502 are used as packaging for perishable goods, such as produce. For example, the produce may include delicate produce items such as strawberries, grapes, peaches, etc. However, it is contemplated that the shipping containers may be used for all types of goods that may be susceptible to damage from vibrations during transport, not just perishable goods. For example, non-perishable goods susceptible to vibrational damage may include, but are not limited to, electronics, building materials, hazardous materials, consumer goods (housewares, appliances, etc.), automobiles, or other commonly transported goods. FIG. 5 further illustrates a portable monitoring device 504. In one embodiment, the portable monitoring device 504 may be the same as the portable monitoring devices 106 described above. As described above, the portable monitoring device 504 may include an accelerometer 506 or other vibration sensing device for monitoring vibrational frequencies and amplitudes experienced by the portable monitoring device 504. Where the portable monitoring device and/or the accelerometer are positioned on a shipping container, the measured monitored vibrational frequencies and amplitudes may be representative of those experienced by the goods within the shipping containers. As shown in FIG. 5, the portable monitoring device 504 is located at the rear-most portion of the transport vehicle (i.e. closest to the loading door), which is generally where the vibrational amplitudes are most significant. However, in some embodiments, multiple additional accelerometers (not shown) may be positioned within the transport vehicle for monitoring vibrational frequencies and amplitudes at various locations throughout the transport vehicle 102.

Figure 6:
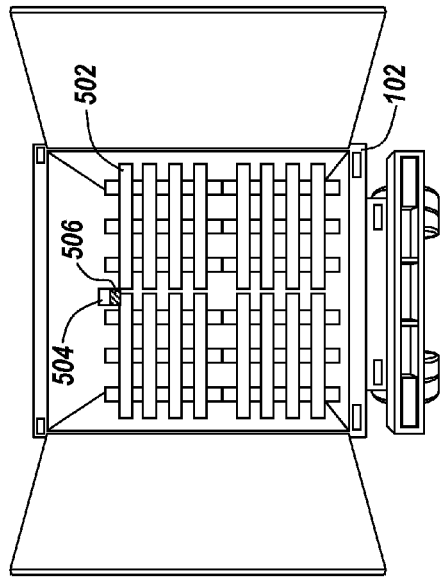
FIG. 6 is a diagram illustrating a possible mounting location for a portable monitoring device in a vehicle for monitoring damage to perishable goods from a back-to-front view of the vehicle.

FIG. 6 illustrates a back-to-front view of the transport vehicle 102, shown with the cargo doors open to view the interior of the transport vehicle 102. A number of shipping containers 502 are shown, along with the portable monitoring device 504 and the accelerometer 506. In one embodiment, the portable monitoring device 504 is positioned at the rear of the transport vehicle and at the top most portion of the shipping containers 502. The portable monitoring device 504 may further be positioned as close to a centerline-axis of the transport vehicle 102 as possible. While the portable monitoring device 504 is shown in one particular location in FIGS. 5-6, it is anticipated that the portable monitoring device 504 may be located anywhere within the transport vehicle where the shipping containers are subjected to the most vibration. While the portable monitoring device 504 may be positioned anywhere within the transport vehicle, it is generally preferable to position the portable monitoring device 504 directly on the shipping containers 502 to get an accurate and representative measurement of the worst-case vibrations that the goods stored in the shipping containers 502 are subjected to during transport. Further, to accurately predict the level of damage to the goods, as described below, it is desirable to position the portable monitoring device 504 as close to highest vibration area as possible. As stated above, additional accelerometers may be used throughout the transport vehicle 102 to provide more accurate measurements throughout the vehicle. The additional accelerometers can communicate directly with the portable monitoring device 504. For example, the portable monitoring device 504 may include a Tx/Rx circuit, such as Tx/Rx circuit 202 described above. The Tx/Rx circuit may allow the portable monitoring device 504 to communicate with the additional accelerometers via a wireless communication network, as described above.

Figure 7:
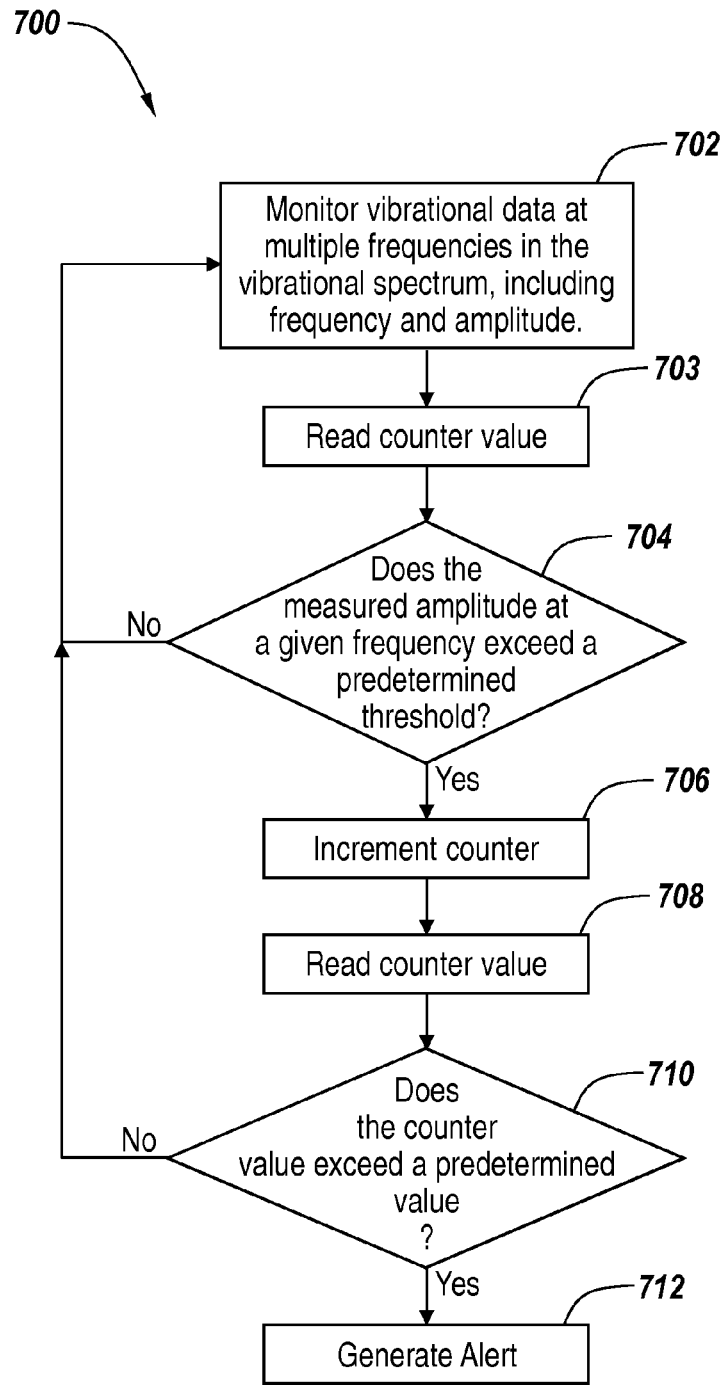
FIG. 7 is a flow chart of a process for determining a percentage of damage to transported goods.

Turning now to FIG. 7, a flow chart illustrating a process 700 for determining a percentage of damage to goods during transport is shown, according to one embodiment. At process block 702, vibrational data is monitored at multiple frequencies. For example, the accelerometer 506 may monitor all frequencies within a given range (e.g. the range of the accelerometer), or the accelerometer 506 may monitor a subset of frequencies. For example, the accelerometer 506 may only monitor those frequencies associated with the most damage to a particular perishable good. The amplitude of vibrations detected at each frequency is also be monitored. In one embodiment, the vibrations are monitored using an accelerometer, such as the accelerometer contained within a portable monitoring device, as described above. The accelerometer may detect vibrations in an X-direction, a Y-direction, and a Z-direction. Further, the accelerometer may monitor both peak amplitude of measured vibrations ($G_{peak}$), as well as an RMS value ($G_{RMS}$). In one embodiment, a processor, such as processor 208 described above, monitors the measured values provided by the accelerometer to evaluate the monitored data. In one embodiment, the monitored vibrational data may be stored in memory, such as memory 210. The monitored vibrational data may be stored in a temporary buffer within the memory. The monitored vibrational data may be stored for predetermined time periods for analysis, such as five minutes. However, predetermined time periods of more than five minutes or less than five minutes are also considered.

Turning briefly now to FIG. 8, a data plot 800 showing an output of a three-axis accelerometer, such as that described above, is shown according to one embodiment. The data plot 800 shows acceleration data at a given frequency for the Z-axis 802, the X-axis 804 and the Y-axis 806. The data plot 800 further shows an interrupt signal line 808. The interrupt signal line 808 may be output from the accelerometer. Alternatively, the interrupt signal line 808 may be generated by a processor, such as described in regards to FIG. 2, above. The interrupt signal line 808 may generate an interrupt signal 810 when the amplitude of a measured vibrational frequency exceeds a pre-determined value. The interrupt signal may be a digital "high" signal as shown in FIG. 8, or a digital "low" signal, depending on the configuration of the processor. For the system illustrated in data plot 800, the frequency of the vibrations being monitored is 25 Hz, and the threshold is 859 $mG_{peak}$. However, these values are exemplary only, and, as described below, the frequencies and threshold values for a given system will be dependent on the type of goods being transported. Furthermore, as will be discussed in more detail below, generally an entire frequency spectrum of the vibration is monitored using the accelerometer to provide greater predictive accuracy of the damage to the goods.

Returning now to FIG. 7, at process block 703, the processor processes the monitored data collected in process block 702. In one embodiment, the processor may use the damage detection module 228, described above, to process the collected data. In one embodiment, the processor may determine an absolute value of the monitored vibrational amplitudes across all three axis. For example, the absolute value of the recorded vibrations may be determined using Equation 1, below.

$$|v|=\sqrt[2]{x^2+y^2+z^2} \qquad \text{Equation 1}$$

Furthermore, at process block 703, the processor may further apply a low pass filter to the vibrational amplitudes monitored in process block 702. For example, the low pass filter may filter out all vibrational amplitudes above 12 Hz. However, frequencies greater than 12 Hz, and frequencies less than 12 Hz are also considered. As will be described in more detail below, the frequencies subjected to low pass filtering may be based on the type of perishable good being monitored.

At process block 704 the processor determines if the measured amplitudes at one or more monitored frequencies, in any of the X-direction, the Y-direction, and/or the Z-direction exceeded a predetermined value. In one embodiment, the processor can determine if the absolute value of the amplitude computed at process block 703 exceeds the predetermined maximum amplitude. In a further embodiment, the predetermined value is a maximum amplitude associated with the perishable goods. In one embodiment, the predetermined value is stored in a memory of a portable monitoring device, such as the portable monitoring device 106, described above. In a further embodiment, the predetermined value is input into the portable monitoring device 506 via a user interface. In other examples, the predetermined value may be input by a user into the remote server 114, which can then transmit the predetermined value to the portable monitoring device 506. In still further examples, a user may be able to input the type of good being monitored to the portable monitoring device 106, which may then set the predetermined value to be monitored based on the type of good.

As described in more detail below, the predetermined maximum amplitude can be determined based on the type of perishable good being monitored. If the processor does not detect a vibrational amplitude that exceeds a predetermined value, the process returns to process block 702 and continues monitoring the vibrational data. If the processor does detect a vibrational amplitude at one or more monitored frequencies that exceeds a predetermined threshold, a counter is incremented at process block 706. In one embodiment, the counter is stored in the memory of a portable monitoring device 506, such as the portable monitoring device 106, described above. In other embodiments, the counter may be stored within a register of a processor of the portable monitoring device.

Additionally, the monitored frequencies in the X-direction, the Y-direction, and/or the Z-direction are measured over one or more monitored frequencies, as described above. In one embodiment, the one or more monitored frequencies may be ranges of frequencies associated with each axis of measurement (e.g. the X-direction, the Y-direction, and/or the Z-direction). In a further embodiment, the ranges of frequencies may be associated with the type of perishable good (or goods in general) being transported. As will be described in more detail below, certain frequency ranges of vibrations may have a more significant impact in regards to damaging the goods than other frequency ranges. Thus, in some embodiments, the range of frequencies monitored may be dependent on the type of good. In one embodiment, a user enters the type of good being transported into the portable monitoring device 506, which may then set the ranges of frequencies to be monitored based on the type of good being transported. In one example, the user enters the type of good being transported directly into the portable monitoring device 506. In other examples, a user may enter the type of good being transported into the remote server 114, which may then be transmitted to the portable monitoring device 506. Further, the user may enter the type of good being transported into the remote server 114, which may then transmit the frequency ranges to be monitored directly to the portable monitoring device.

Turning briefly to FIG. 9, an illustration of a counter registry 900 is shown according to one embodiment. As shown in FIG. 9, interrupt counter register 902, (INT1_CFG) is the counter associated with a detected amplitude of a frequency over a threshold value. While interrupt counter register 902 is the only interrupt counter in FIG. 9 shown as associated with an amplitude of a frequency of exceeding a predetermined value vibration (e.g. the absolute value computed in process block 703), multiple counters associated with different predetermined values are contemplated. For example, there may be a counter for each of the Z-axis, the Y-axis, and the X-axis. In still further examples, there may be a counter for a number of frequencies, or ranges of frequencies, of vibration. However, the above use of a single counter 902 to count every vibrational frequency exceeding a predetermined amplitude may be utilized to reduce the amount of data that is required to be stored and/or transmitted using a portable monitoring device, as described above.

The process 700 then reads the counter value at process block 708. In some examples, the counter value is read after every instance of the counter being incremented. In one embodiment, the counter value is read at predetermined intervals. For example, the counter value may be read every five seconds. However, predetermined intervals of more than five seconds or less than five seconds are further contemplated. In other examples, the counter value may be read during each scan cycle of a processor, such as the processor 208 described above in FIG. 2. Once the counter value is read at process block 708, the counter value is evaluated to determine if the counter value exceeds a predetermined counter value at process block 710. In one embodiment, the predetermined counter value may be stored in the damage threshold information 408, as described above. In one embodiment, the predetermined counter value can be a value associated with a certain level of damage to the goods being transported, as will be described in more detail below. In a further embodiment, the predetermined counter value is stored in the memory of a portable monitoring device, such as the portable monitoring device 106, described above. If the counter value does not exceed the predetermined counter value, the process 700 returns to monitoring vibrational data at process block 702. If the counter value is determined to exceed the predetermined counter value, an alert may be generated at process block 712. In some embodiments, multiple predetermined counter values for each axis are provided. Each of the multiple predetermined counter values may be associated with a level of damage to the goods being transported. The multiple predetermined counter values may be specific to the type of good being transported, as described below.

In one embodiment, the alert is generated and transmitted to a remote server, such as remote server 114 described above. The remote server 114 may then send a message to the driver or company associated with the transport vehicle 102 to inform them that damage is starting to occur to the goods being transported. For example, the remote server 114 may use the damaged goods module 320 to determine whether to issue the message to the driver or company. In other embodiments, the alarm may be stored in the portable monitoring device for accessing when the goods are delivered to the destination. The generated alerts may then be accessed to determine what the percentage of damage of the goods is likely to be. In some examples, the generated alerts may include an estimated percentage of damage to the goods. In some embodiments, the alert may include other data such as when the alarms were generated, at what location, etc. For example, the alarm data may include data from the location module to show where along the route the alarm(s) occurred, as well as other information such as speed of the transport vehicle and trip duration. In one embodiment, the alarm data may be stored with the damaged goods module 320, within the memory 304 of the remote server 114.

In some embodiments, multiple alarms may be generated where the counter exceeds multiple predetermined counter values of increasing value. For example, the predetermined counter value used in process block 710 may be one of multiple predetermined counter values, where each predetermined counter value indicates a further degree of damage to the goods being transported. For example, the predetermined counter values may correlate to 10% damage, 25% damage, 40% damage and 50% damage, etc. However, multiple configurations are contemplated. In one embodiment, a user may be able to select the predetermined counter values which generate an alarm, and what the associated damage percentage would then be for each alarm.

Figure 10:
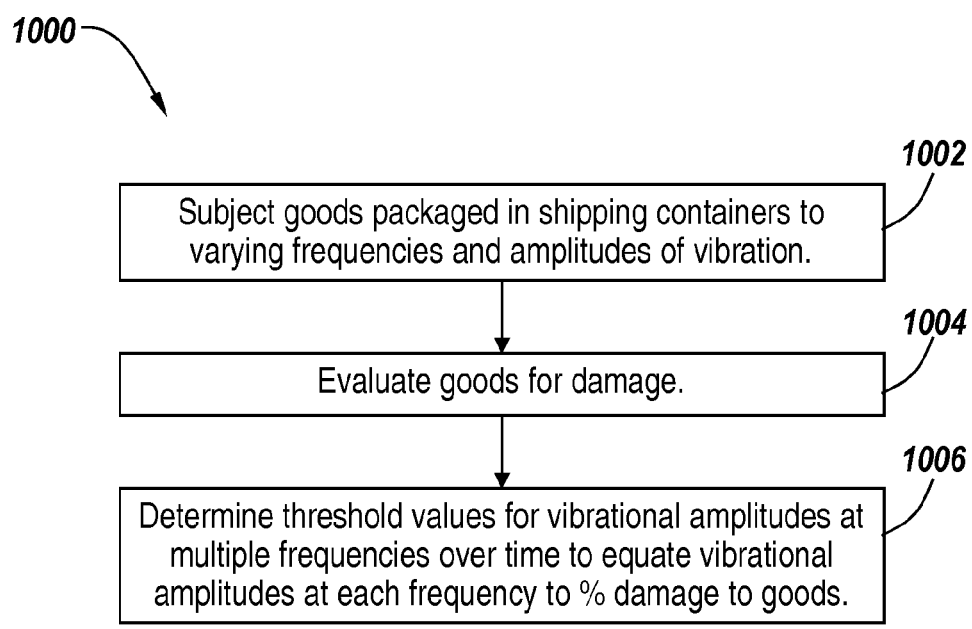
FIG. 10 is a flow chart of a process for alerting a user that damage to goods has exceeded or is about to exceed a predetermined threshold.

Turning now to FIG. 10 a process 1000 for determining threshold values for amplitudes of vibrational frequencies and predetermined counter values is described, according to one embodiment. At process block 1002 goods are packaged and placed in shipping containers as they would be during transit. The goods are then subjected to vibrations at varying frequencies and at varying amplitudes. At process block 1004, the goods are then evaluated for damage. In some embodiments, the goods are evaluated based on the percentage of the product that would be deemed unsalable. For some products, USDA guidelines may be used to determine the level of damage, such as when the goods are deemed unsalable. Or, USDA guidelines may be used to show when sufficient damage has been done to result in a USDA grade reduction. However, other standards, such as those set by the distributor and/or purchaser may be used to determine the levels of damage to the goods, and/or when the goods become unsalable. Examples of this determination for various goods are provided below. Finally, at process block 1006 the threshold values for vibrational amplitudes at one or more frequencies over time can be determined which equate to a percentage of damage to the goods. The process 1000 can be executed multiple times to allow for damage to be evaluated across multiple frequencies, amplitudes and time periods.

Figure 11:
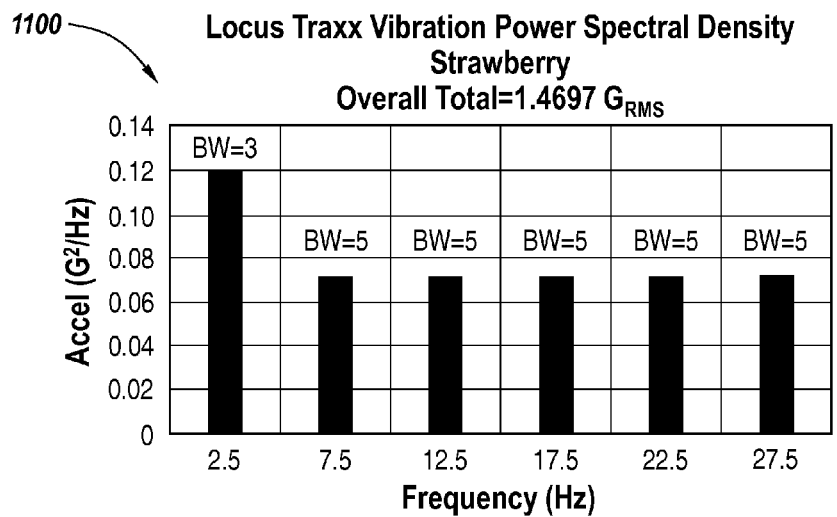
FIG. 11 is a graph illustrating exemplary measurements taken with regards to the vibrational spectrum density as applied to strawberries during simulated transport.

FIGS. 11-14 provide exemplary illustrations of determining threshold values using the process 1100 described above for various perishable goods. The results shown in FIGS. 11-14 are based on a study entitled "Simulated In-Transit Vibration Damage to Packaged Fresh Market Grapes and Strawberries," conducted by D. Fischer, W. L. Craig, A. E. Watada, W. Douglas, and B. H. Henry. However, it is understood that analysis for determining damage levels of other perishable goods could be conducted using the processes described in FIGS. 10-14. FIG. 11 illustrates a vibration spectral density plot 1100 that was applied to a perishable good. In this example, the perishable goods were strawberries. As shown in the chart, a primary vibration component having a frequency range of 2-5 Hz was applied at an acceleration rate of approximately 0.12 $G^2/Hz$. The primary vibration component further had a bandwidth of 3 Hz, although bandwidths of greater than 3 Hz or less than 3 Hz are also considered. Additionally, secondary vibrational frequency ranges of 5-10 Hz, 10-15 Hz, 15-20 Hz, 20-25 Hz and 25-30 Hz were also applied at an acceleration rate of about 0.07 $G^2/Hz$. The secondary vibration components had a bandwidth of about 5 Hz. The total amplitude applied was equal to 1.4697 $G_{RMS}$ across all the frequencies. In one embodiment, the vibrations were applied to the strawberries for 30 minutes. However, time periods of less than 30 minutes or greater than 30 minutes are contemplated. The values described above are exemplary only, and it is contemplated that multiple other frequencies, amplitudes and bandwidths may be used, as required.

Figure 12:
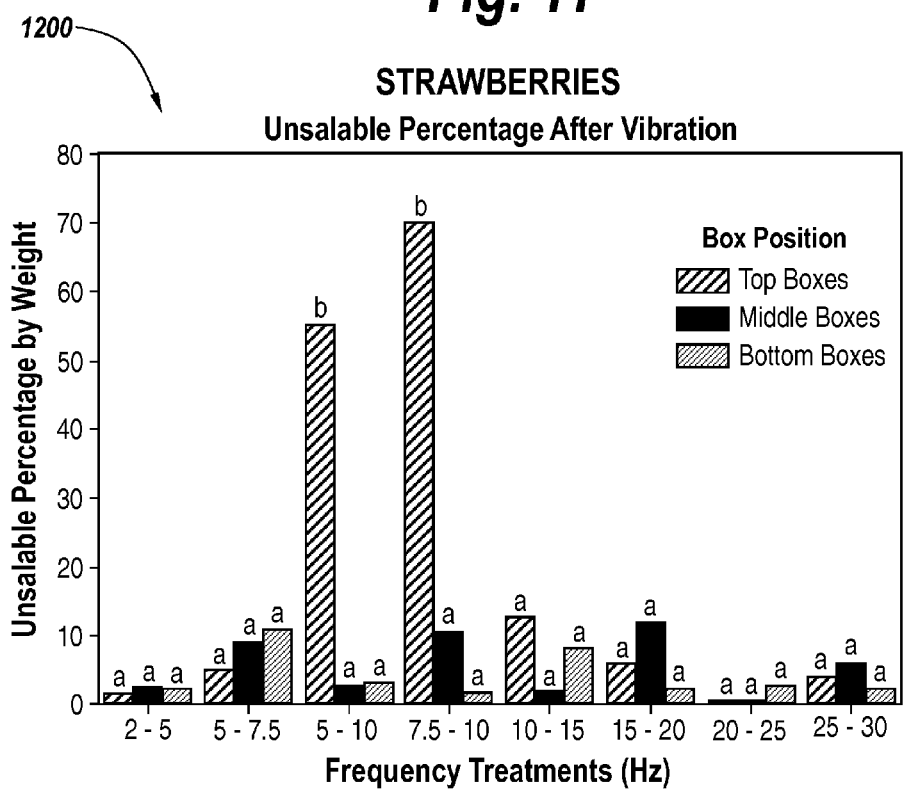
FIG. 12 is a distribution chart showing percentage by weight of unsalability of strawberries, based on location and applied frequencies during simulated transport.

Turning now to FIG. 12 a distribution plot 1200 showing the unsalable percentage by weight of the strawberries subjected to the vibrations described in FIG. 11 is shown, according to one embodiment. For each frequency range (X-axis) the products were evaluated based on their position in the packaging. In this example, the results were divided by the "top boxes," the "middle boxes," and the "bottom boxes," similar to how the strawberries would be packaged during shipment. For example, strawberries may typically be packaged in boxes stacked fifteen rows high. While damage to the strawberries was determined across the entire frequency spectrum, and for each position (i.e. top boxes, middle boxes, bottom boxes.), it is clear in the distribution plot 1200 that the strawberries located in the top boxes experienced significant damage in the 5-10 Hz range, as well as in the 7.5-10 Hz range, which showed approximately 70% unsalable strawberries by weight. Thus, monitoring the upper-most portion of the shipping container may be a significant factor in determining where to position the portable monitoring device and/or accelerometers in the transport vehicle. While the strawberries may be evaluated using multiple criteria, Table 1, below, shows the criteria used to evaluate the strawberries in the analysis shown in FIG. 12.

TABLE 1

Strawberry Damage Grading Criteria

| Damage Level | Criteria |
| --- | --- |
| Undamaged | Berries with no abrasions, but may have up to two bruises less than 2 mm in diameter. |
| Slightly Damaged | Berries with no abrasions; but may have up to four bruises less than 2 mm in diameter. |
| Moderately Damaged | Less than 25% of the berry bruised or moderate abrasions covering less than 25% |
| Severely Damaged (Unsalable) | Any berries with bruises or abrasions which penetrated the surface of the fruit. |
| Very Severely Damaged (Unsalable) | Entire fruit bruised, mold formation or pieces of fruit missing. |

Using the results gathered in FIGS. 11 and 12, above, the amplitude thresholds and predetermined counter values can be calculated. Based on the results shown in FIG. 12, the predetermined threshold values can be set to 849 $G_{peak}$ (or 0.6$G_{rms}$). In one embodiment, the threshold value can be determined by integrating the vibration power spectral densities measured at each frequency to determine a Grms value. For example, the vibration power spectral densities shown in FIG. 11. In other embodiments, such as shown above, the threshold value can be peak value calculated by multiplying the square root of two times the Grms ($\sqrt{2}$*Grms=Gpeak). Furthermore, assuming the sampling rate of a processor, such as the processor 208 in the portable monitoring device 106 described above, is 1 sample/80 ms, the predetermined counter values indicating damage to the goods can be determined using Equation 2, below.

If Count>0.03*$P$/0.08; then Fail                        Equation 2

Where Count is equal to the number of recorded peak values of the vibrations at a given frequency, P is equal to the measurement period in seconds, and 0.03 represents 30% damage to the goods. For example, assuming a fifteen minute measurement period, the predetermined number of counts would need to be below three hundred thirty seven to pass.

Figure 13:
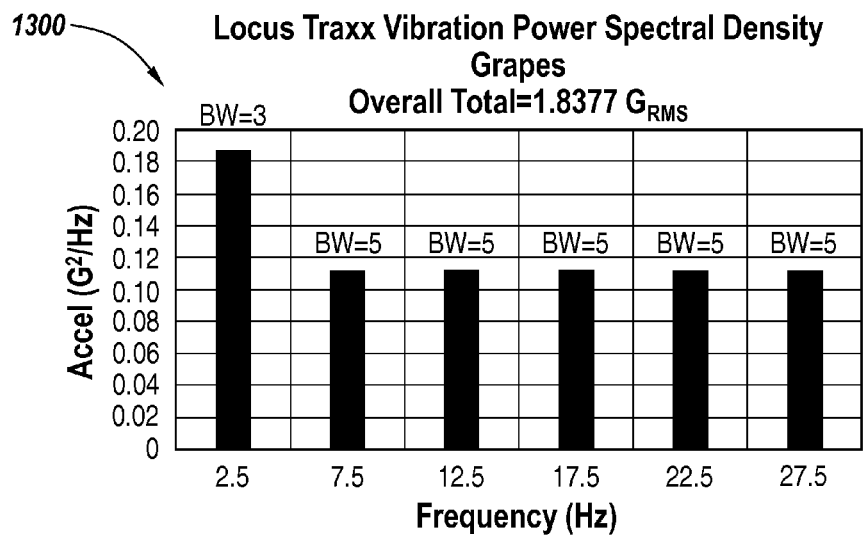
FIG. 13 is a graph illustrating exemplary measurements taken with regards to the vibrational spectrum density as applied to grapes during simulated transport.

FIG. 13 illustrates a further example, wherein the perishable goods are grapes. FIG. 13 includes a vibration spectral density plot 1300 that was applied to multiple containers of fresh grapes. In this example, as above, the grapes were first packaged as they would be for transport. As shown in the chart, a primary vibration component having a frequency range of 2-5 Hz was applied at an acceleration rate of approximately 0.19 $G^2/Hz$. The primary vibration component further had a bandwidth of 3 Hz, although bandwidths of greater than 3 Hz or less than 3 Hz are also considered. Additionally, secondary vibrational frequency ranges of 5-10 Hz, 10-15 Hz, 15-20 Hz, 20-25 Hz and 25-30 Hz were also applied at an acceleration rate of about 0.11 $G^2/Hz$. The secondary vibration components had a bandwidth of about 5 Hz. The total amplitude applied was equal to 0.75 $G_{RMS}$ across all the frequencies. In one embodiment, the vibrations were applied to the grapes for sixty minutes. However, time periods of less than sixty minutes or greater than sixty minutes are contemplated. The values described above are exemplary only, and it is contemplated that multiple other frequencies, amplitudes and bandwidths may be used, as applicable.

Figure 14:
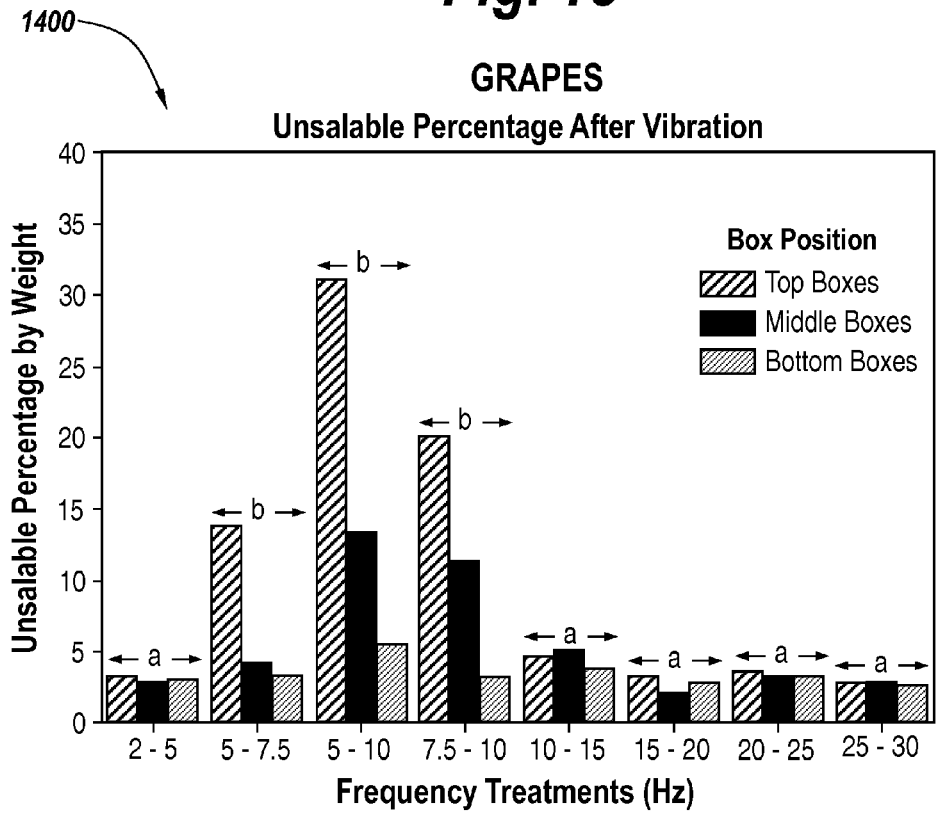
FIG. 14 is a distribution chart showing percentage of weight of unsalability of grapes based on location and applied frequencies during simulated transport.

Turning now to FIG. 14 a distribution plot 1400 showing the unsalable percentage by weight of the grapes subjected to the vibrations described in FIG. 13 is shown, according to one embodiment. For each frequency range (X-axis) the products were evaluated based on their position in the packaging. In this example, the results were divided by the "top boxes," the "middle boxes," and the "bottom boxes," similar to how the grapes would be packaged during shipment. For example, grapes may typically be packaged in boxes stacked nine rows high. While damage to the grapes was determined across the entire frequency spectrum, and for each position (i.e. top boxes, middle boxes, bottom boxes.), it is clear in the distribution plot 1400 that the grapes located in the top boxes experienced significant damage in the 5-7.5 Hz range, the 5-10 Hz range and the 7.5-10 Hz range. In this example, the damage to the grapes was evaluated based on the percentage of shattered grapes by weight. The level of damage to grapes can further impact salability, as 12% shattering of the grapes by weight may result in a USDA grade level reduction.

Based on the results shown in FIG. 14, the predetermined threshold values can be set to 1.061 $G_{PEAK}$ (or 0.75 $G_{rms}$). In one embodiment, the threshold value can be determined by integrating the vibration power spectral densities measured at each frequency to determine a Grms value. For example, the vibration power spectral densities shown in FIG. 13. In other embodiments, such as shown above, the threshold value can be peak value calculated by multiplying the square root of two times the $G_{rms}$ ($\sqrt{2}*Grms=Gpeak$). Furthermore, assuming the sampling rate of a processor, such as the processor 208 in the portable monitoring device 106 described above, is 1 sample/second, the predetermined counter values indicating damage to the goods can be determined using Equation 3, below.

$$\text{If Count} > 0.03*P; \text{ then Fail} \qquad \text{Equation 3}$$

Where Count is equal to the number of recorded peak values of the vibrations at a given frequency, P is equal to the measurement period in seconds, and 0.03 represents 30% damage to the goods. For example, assuming a fifteen minute measurement period, the predetermined number of counts would need to be below twenty-seven to pass.

While the above analysis was done in regards to strawberries and grapes, it is contemplated that the above processes may be used to provide an understanding of the effects of vibrations across multiple frequencies and amplitudes may have on perishable goods. This data may then be used to monitor similar perishable goods in transit to provide data and/or alerts relating to potential damage to the goods. This data can be used to help determine better routes for transportation, better packaging solutions, and/or other modifications relating to the transport of perishable goods to reduce the damage caused by vibration during transportation.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, orientations, etc.). By way of example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on memory or other machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products or memory comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, by way of example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method for estimating a level of damage to perishable cargo during transportation of the cargo using data collected by a portable monitoring device, the method comprising:
    receiving an input indicative of a frequency range of interest;
    measuring vibrational data occurring within the frequency range of interest, the vibrational data associated with the cargo, the vibrational data monitored by a vibration sensor of the portable monitoring device;
    incrementing a counter in the portable monitoring device in response to an amplitude of the measured vibrational data exceeding a predetermined threshold;
    determining if value of the counter exceeds a predetermined value; and
    generating an alert indicating damage to the cargo in response to determining the value has exceeded the predetermined value.

2. The method of claim 1, wherein the vibrational data includes amplitude data across a spectrum of frequencies of vibration.

3. The method of claim 2, further comprising setting the spectrum of frequencies of vibration to be monitored based on a type of cargo being monitored.

4. The method of claim 1, wherein the vibrational data includes vibrational data across three axes of vibration.

5. The method of claim 1, further comprising generating an interrupt using a processing circuit of the portable monitoring device, in response to determining the amplitude of the measured vibrational data has exceeded the predetermined threshold.

6. The method of claim 1, further comprising transmitting the value to a remote server using the portable monitoring device.

7. The method of claim 1, wherein the predetermined value represents an expected level of damage to the cargo.

8. The method of claim 1, further comprising transmitting the generated alert to a remote server using the portable monitoring device.

9. The method of claim 1, wherein the generated alert comprises an estimated percentage of damage to the cargo.

10. A system for determining a level of damage to perishable goods during transport, the system comprising:
an accelerometer configured to receive an input indicative of a frequency range of interest and measure vibrations occurring within the frequency range of interest transmitted to the perishable goods during transport;
a processing circuit comprising a memory and a processor, the processing circuit in communication with the accelerometer and configured to receive vibrational data associated with the measured vibrations from the accelerometer;
the processing circuit configured to generate an interrupt when an amplitude of the received vibrational data exceeds a predetermined threshold, the interrupt incrementing a counter value stored in the memory;
the processing circuit further configured to generate an alert in response to determining the counter value has exceeded a predetermined value; and
a portable monitoring device configured to attach to at least one of the perishable goods, a housing containing the perishable goods, and a pallet on which the perishable goods are placed, the portable monitoring device including the processing circuit.

11. The system of claim 10, wherein the predetermined value represents an expected level of damage to the perishable goods.

12. The system of claim 10, wherein the predetermined value is dependent on the type of perishable good.

13. The system of claim 10, wherein the accelerometer is further configured to monitor one or more frequency ranges across a first axis, a second axis, and a third axis, wherein the frequency ranges dependent on the type of perishable good being monitored; and
wherein the processing circuit is further configured to change an operation related to power consumption by the portable monitoring device in response to a low power situation with the portable monitoring device to ensure enough power remains for a duration of a scheduled trip.

14. The system of claim 13, wherein the vibrational data includes an amplitude for each of a plurality of frequency ranges.

15. The system of claim 13, wherein the predetermined threshold is user configurable.

16. The system of claim 10, wherein the processing circuit further comprises a transmit/receive circuit configured to provide wireless communication to a remote server, wherein the portable monitoring device is configured to transmit the alert to the remote server using the transmit/receive circuit.

17. The system of claim 10, wherein the accelerometer is integrated into the portable monitoring device.

18. A method of determining a level of damage to perishable cargo due to vibrations occurring during transport, the method comprising:
receiving an input indicative of a frequency range of interest;
measuring vibrational data occurring within the frequency range of interest using a vibration sensor attached to at least one of the perishable cargo, a container containing the perishable cargo, and a pallet on which the perishable cargo is placed, the vibrational data including an amplitude measurement of the vibrations at each of a plurality of predetermined frequency ranges;
transmitting the vibrational data to a processing circuit of a portable monitoring device;
determining if the vibrational data exceeds a threshold value associated with damage occurring to the perishable cargo using the processing circuit of the portable monitoring device;
generating an interrupt signal for every occurrence of the threshold value being exceeded using the portable monitoring device;
incrementing a counter in the portable monitoring device for every interrupt signal generated;
determining if a value of the counter exceeds a first predetermined value within a predetermined time period; and
generating an alert indicating a first level damage to the cargo in response to determining the value has exceeded the first predetermined value.

19. The method of claim 18, further comprising:
determining if the value exceeds a second predetermined value within the predetermined time period; and
generating a second alert indicating a second level of damage to the cargo in response to determining the value has exceeded the second predetermined value.

20. The method of claim 18, wherein the vibration sensor is attached to the container at a location experiencing the greatest amount of vibration during transport.

* * * * *